United States Patent [19]
Reiss

[11] Patent Number: 4,966,604
[45] Date of Patent: Oct. 30, 1990

[54] EXPANDABLE ATHERECTOMY CUTTER WITH FLEXIBLY BOWED BLADES

[75] Inventor: Robert E. Reiss, La Jolla, Calif.

[73] Assignee: InterVentional Technologies Inc., San Diego, Calif.

[21] Appl. No.: 299,148

[22] Filed: Jan. 23, 1989

[51] Int. Cl.⁵ .............................................. A61B 17/32
[52] U.S. Cl. ..................................... 606/159; 606/170; 606/180; 604/22
[58] Field of Search .............. 606/159, 170, 167, 180, 606/160, 127, 113, 198; 604/22; 128/751, 752

[56] References Cited

U.S. PATENT DOCUMENTS

| | | | |
|---|---|---|---|
| 2,556,783 | 6/1951 | Wallace | 606/127 |
| 2,729,210 | 1/1956 | Spencer | 128/2 |
| 2,730,101 | 1/1956 | Hoffman | 606/159 |
| 2,749,909 | 6/1956 | Ullery et al. | 128/2 |
| 3,320,957 | 5/1967 | Sokolik | 606/170 X |
| 3,512,519 | 5/1970 | Hall | 128/2 |
| 3,605,721 | 9/1971 | Hallac | 128/2 |
| 3,815,604 | 6/1974 | O'Malley et al. | 128/305 |
| 3,990,453 | 11/1976 | Douvas et al. | 128/305 |
| 4,273,128 | 6/1981 | Lary | 128/305 |
| 4,320,762 | 3/1982 | Bentov | 128/343 |
| 4,441,509 | 4/1984 | Kotsifas et al. | 128/757 |
| 4,589,412 | 5/1986 | Kensey | 128/305 |
| 4,598,710 | 7/1986 | Kleinberg et al. | 128/318 |
| 4,610,662 | 9/1986 | Weikl et al. | 604/53 |
| 4,627,436 | 12/1986 | Leckrone | 128/303 |
| 4,631,052 | 12/1986 | Kensey | 604/22 |
| 4,636,195 | 1/1987 | Wolinsky | 604/53 |
| 4,640,296 | 2/1987 | Schnepp-Pesch et al. | 128/754 |
| 4,646,738 | 3/1987 | Trott | 128/305 |
| 4,650,466 | 3/1987 | Luther | 606/198 X |
| 4,653,496 | 3/1987 | Bundy et al. | 128/305 |
| 4,655,217 | 4/1987 | Reed | 128/305 |
| 4,655,771 | 4/1987 | Wallsten | 623/1 |
| 4,664,112 | 5/1987 | Kensey et al. | 128/341 |
| 4,665,918 | 5/1987 | Garza et al. | 128/343 |
| 4,669,469 | 6/1987 | Gifford, III et al. | 128/305 |
| 4,679,557 | 7/1987 | Opie et al. | 128/305 |
| 4,685,458 | 8/1987 | Leckrone | 128/303 |
| 4,686,982 | 8/1987 | Nash | 128/305 |
| 4,690,140 | 9/1987 | Mecca | 128/305 |
| 4,696,667 | 9/1987 | Masch | 604/22 |
| 4,706,671 | 11/1987 | Weinrib | 606/159 |
| 4,708,147 | 11/1987 | Haaga | 128/753 |
| 4,728,319 | 3/1988 | Masch | 604/22 |
| 4,732,154 | 3/1988 | Shiber | 128/305 |
| 4,754,755 | 7/1988 | Husted | 128/305 |
| 4,757,826 | 7/1988 | Abdulhay | 128/757 |
| 4,765,332 | 8/1988 | Fischell et al. | 128/305 |
| 4,895,560 | 1/1990 | Papantonakos | 604/22 |

OTHER PUBLICATIONS

Coronary Artery Incision and Dilation, B. G. Lary, M.D., Archives of Surgery, Dec. 1980, vol. 115, pp. 1478–1480.

Method for Increasing the Diameter of Long Segments of the Coronary Artery, B. G. Lary, M.D., The American Surgeon, Jan. 1966, vol. 32, No. 1, pp. 33–35.

A Method for Creating a Coronary-Myocardial Artery, B. G. Lary, M.D., et al., Surgery, St. Louis, vol. 59, No. 6, pp. 1061–1064.

*Primary Examiner*—Michael H. Thaler
*Attorney, Agent, or Firm*—Nydegger & Harshman

[57] ABSTRACT

An expandable atherectomy cutting device comprises a flexible blade having one end connected to a torque tube and the other end connected to a tip. The tip and torque tube are rotatably positioned about a guide wire, and the torque tube is coupled to a drive element for rotating the flexible blade about the guide wire. A mechanism is associated with the tip and torque tube for pulling the tip toward the torque tube to cause the flexible blade to bow outwardly away from the guide wire to expand its radius of cutting action. The mechanism for causing the flexible blade to bow outwardly includes a base rotatably mounted in slidable relation in the torque tube, and a series of desmodromic filaments connecting the base to the tip for pulling the tip toward the torque tube. The flexible blade includes a bend so that it bows outwardly rather than inwardly. The amount of expansion is controlled by a control element coupled to the drive element so that it can be controllably expanded through an infinite variety of positions within a continuous range, and further, can be expanded while the blade is rotating.

2 Claims, 2 Drawing Sheets

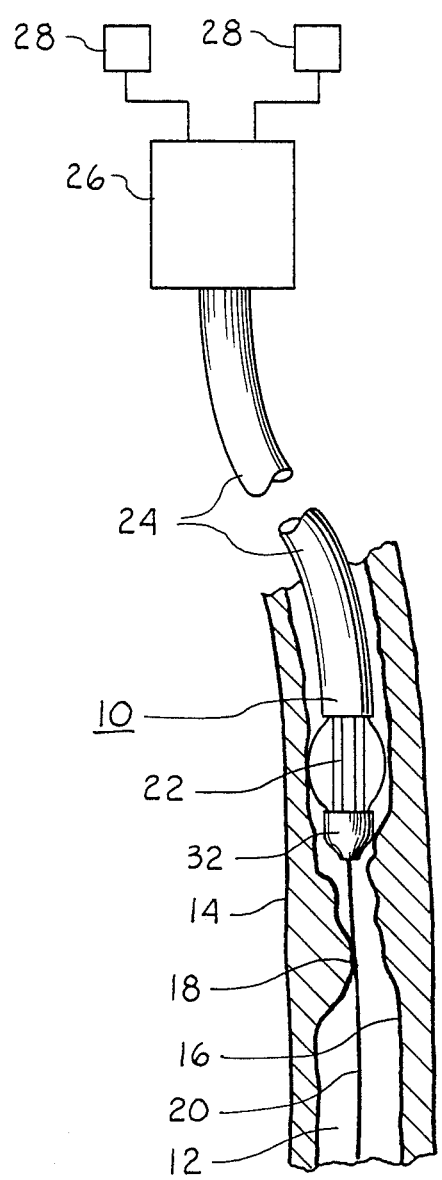
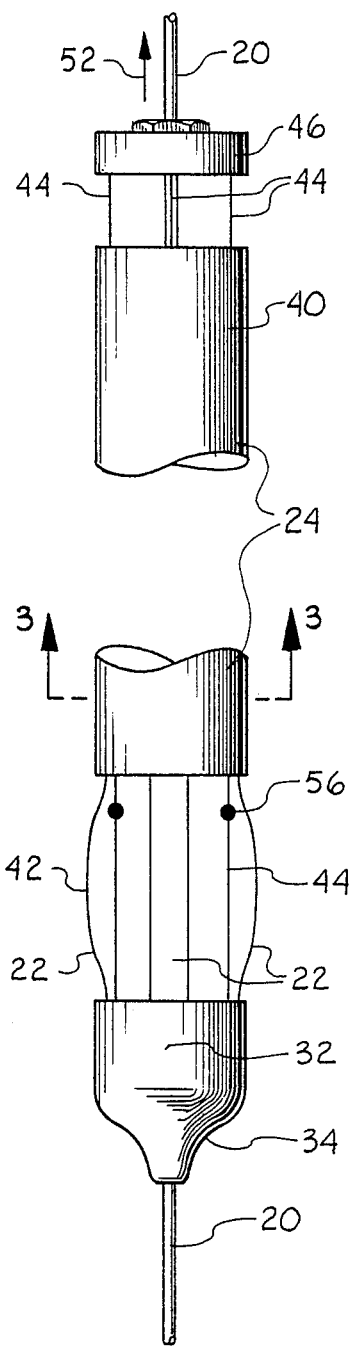
Fig. 1
Fig. 2

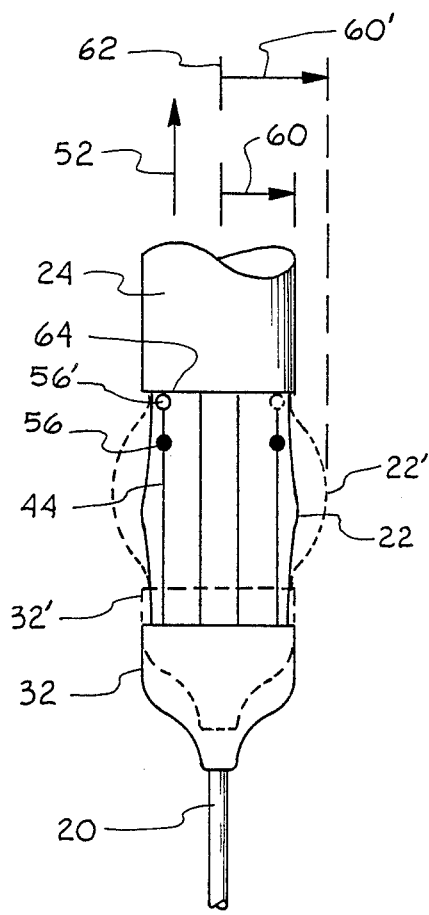

EXPANDABLE ATHERECTOMY CUTTER WITH FLEXIBLY BOWED BLADES

FIELD OF THE INVENTION

This invention relates generally to atherectomy cutter devices. More particularly, this invention relates to a rotating atherectomy cutter which permits controllable expansion of its cutting action while in operation. This invention is particularly, but not exclusively, useful for atherectomy procedures wherein it is desirable to cut an opening through obstructive tissue in the lumen of a body vessel that is larger than the maximum normal cross-sectional area of the atherectomy device itself.

BACKGROUND OF THE INVENTION

Various means and procedures have been developed in recent years to clear or open occluded arteries and other body vessels in order to restore the necessary circulation of blood through the body. In many situations, such intravessel procedures are preferable to "bypass" operations in which the affected vessel is effectively shunted because intravessel procedures can be relatively quickly performed and do not require an incision into the chest cavity or some other part of the body. Consequently, various procedures and several different devices for performing these procedures have been developed.

In general, there are three ways to eliminate or ameliorate the difficulties caused by an occlusion in an artery. First, it may be possible to dissolve the obstructive tissue causing the occlusion by the ingestion or injection of properly selected medicaments. Such treatment, however, may be ineffective due to an excessive time for response or undesirable due to adverse side effects. Second, well known angioplasty procedures may be used. With the angioplasty procedures, however, the obstructive tissue causing the occlusion remains in situ after the procedure is performed. Thus, the problem may be compromised but it is not eliminated and there remains the real probability there will be a restenosis. Third, atherectomy related procedures may be performed.

In any atherectomy procedure, the obstructive tissue causing the occlusion in the vessel (or at least a part of this obstructive tissue) is cut or clipped from the lumen of the vessel. As should be readily apparent, the instruments used for this purpose require specifically designed cutting devices. Further, the devices which are used for controlling the position of the cutting device in the lumen require special fabrication and design considerations. Specifically, both the cutting device itself and whatever control elements are inserted into the vessel with the cutting device must be miniaturized.

Several atherectomy related devices have been previously disclosed. Exemplary of such devices is Husted U.S. Pat. No. 4,754,755 which discloses a catheter with a cylindrical rotary blade that is used to clear arterial obstructions. As another example of an atherectomy device, Shiber U.S. Pat. No. 4,732,154 discloses a rotary catheter system for this same purpose. For each of the devices disclosed in these references, however, the effective cutting area of the blade of the device is limited. This is so because, in these typical devices, the cutting action of the rotating blade is not capable of extending beyond the periphery of the tubular structure which is used to introduce the blade into the vessel. Consequently, the effective cutting area of the blade is limited by the size of the support structure and this support structure, in turn, is limited to the maximum permissible size of the opening that can be used for an entry site. It often happens, however, that the maximum permissible size of the opening for an entry site is smaller than the cross-sectional area of the vessel lumen at the location where the atherectomy cutter is to be operated. Thus, there is a need for an expandable cutter.

The present invention recognizes the need for an atherectomy cutter which can be expanded, once it is positioned within the lumen of a body vessel, to increase the cutting effectiveness of the device. Further, the present invention recognizes the need for a cutter which can have its cutting action expanded through an infinite variety of diameters between given upper and lower limits while the blades are rotating.

In light of the above, it is an object of the present invention to provide a cutter for an atherectomy device which can be expanded once it is inside the lumen of a body vessel. Another object of the present invention is to provide an atherectomy device which can be adjustably expanded to an infinite variety of settings between upper and lower limits as required to excise obstructive tissue from inside the lumen of a body vessel. Still another object of the present invention is to provide an atherectomy device which can be effectively controlled during the cutting of obstructive tissue from the inside of a body vessel. Yet another object of the present invention is to provide an atherectomy device which is easy to use, relatively easy to manufacture and comparatively cost effective.

SUMMARY OF THE INVENTION

A preferred embodiment of the expandable atherectomy cutting device comprises a flexible blade having a first end connected to a tip and a second end connected to a torque tube, the tip and torque tube being coupled for combined rotation about a guide wire. A controlling drive mechanism is attached to the torque tube for rotating the flexible blade about the guide wire. Associated with the tip and torque tube is a mechanism for urging the tip toward the torque tube to cause the flexible blade to bow outwardly away from the guide wire to provide an expanded cutting path. The tip itself is urged by the flexible blade toward and into a first position where the blade defines a first radius of cutting action. The mechanism for pulling the tip away from the first position and toward the torque tube includes a base rotatably mounted in slidable relation with the torque tube. Desmodromic filaments are connected between the base and the tip for pulling the tip toward and into a second position in which the blade defines a second radius of cutting action greater than the first radius of cutting action.

Also included is a suction mechanism for removing unwanted debris. The cutting device of the present invention can be inserted into a desired body vessel while the device is configured with its first radius and moved through the vessel to the desired site of operation. After being positioned at the desired site of operation, the cutting device can then be controllably expanded into the configuration with its larger second radius for cutting obstructive tissue from the lumen of the vessel as desired.

The novel features of this invention, as well as the invention itself, both as to its structure and its operation, will be best understood from the accompanying draw-

BRIEF DESCRIPTION OF THE DRAWINGS

FIG. 1 is a schematic illustration of the expandable atherectomy cutting device of the present invention in its intended environment;

FIG. 2 is a side view of the expandable atherectomy cutting device of the present invention;

FIG. 3 is a cross-sectional view taken along line 3—3 of the expandable atherectomy cutting device shown in FIG. 2; and FIG. 4 is a schematic illustration of the expandable atherectomy cutting device moving between a first position and a second position.

DESCRIPTION OF THE PREFERRED EMBODIMENTS

Referring now to FIG. 1 there is shown an expandable atherectomy cutting device, generally designated 10, in its intended environment. The cutting device 10 is shown inserted into the lumen 12 of a vessel 14. On the inner wall 16 of vessel 14 is a lesion 18 (i.e. obstructive tissue) which is an unwanted volume of material that has attached to the inner wall 16 of vessel 14. For purposes of the present invention, vessel 14 may be an artery or any other lumen from which it is necessary to cut away an unwanted volume of material. For example, lesion 18 may be plaque or some other substance which has created an occlusion in the lumen of an artery. Further, lesion 18 may be a growth, or some other similar occluding obstruction which needs to be removed from the inner wall 16 of vessel 14.

Regardless of the type of vessel 14, or the type of lesion 18, it is desired that some or all of the lesion 18 be cut away by cutting device 10. This is accomplished by cutting device 10 substantially as follows. First a guide wire 20 is inserted into lumen 12 of vessel 14 by a procedure well known in the pertinent art. Cutting device 10 is then positioned over guide wire 20 and is slidingly moved along the guide wire 20 until device 10 is urged into contact with lesion 18. The rotating blades 22 of device 10 are driven via a torque tube element 24 which is operatively engaged to a control element 26. Control element 26 is coupled to a drive mechanism 28 which imparts a force on torque tube 24 which rotates the blades 22 about the guide wire 20. Also coupled to control element 26 is a suction mechanism 30 for removing unwanted material which has been cut away from lesion 18 in a manner which will be further described below.

Referring now to FIG. 2, there are shown the detailed components of cutting device 10. In particular, device 10 comprises a tip 32 which is rotatably positioned about guide wire 20. Tip 32 is the leading edge of cutting device 10 and preferably has a generally tapered front surface 34 to ease movement of the cutting device through the vessel 14 along guide wire 20. In the preferred embodiment, the tip 32 has a circular cross section. Also rotatably positioned about the guide wire 20 is the torque tube 24 which is hollow and generally cylindrical in shape. Preferably, torque tube 24 has the same outer diameter as that of tip 32. Connected between tip 32 and the distal end of torque tube 24 is a plurality of flexible blades 22 of a suitable material and thickness for cutting away unwanted tissue. In the embodiment shown, there are four generally flat flexible blades 22 positioned about the guide wire 20 at approximately 90° from one another. Each flexible blade 22 has one end attached to tip 32 and another end attached to torque tube 24. Each flexible blade 22 preferably has a bend 42, as substantially shown in FIG. 2, to assure that operation of the device causes each resilient flexible blade 22 to bow outwardly, rather than inwardly, as will be further described below. The flexible blades 22 are attached between tip 32 and torque tube 24 so that the maximum distance between the bends 42 of diametrically opposed blades 22 is the same, or preferably a small amount less than, the outside diameter of torque tube 24 and tip 32. The purpose of this desired configuration will become apparent later in the description.

Connected to the tip 32, at points preferably adjacent the location where each flexible blade 22 is connected to tip 32, is a desmodromic filament 44 for providing a tethered action for the tip 32. Each filament 44 also passes through the sidewall 40 of torque tube 24 and is connected to a base 46 which is rotatably mounted in slidable relation in torque tube 24. On each filament 44 there is included a stop 56 which limits the distance tip 32 can move toward torque tube 24. Base 46 moves in the direction of arrow 52 along torque tube 24.

The position of the hollow torque tube 24 about guide wire 20 can be further appreciated with reference to FIG. 3. Also, as shown in FIG. 3, there are corresponding channels 54 in sidewall 40 of torque tube 24 through which each filament 44 may be slidably carried to provide added protection for filaments 44, and to maintain appropriate positioning of the filaments 44 with respect to the base 46 and tip 32.

OPERATION

Referring now to FIG. 4, there is shown a schematic illustration of the operation of the cutting device 10 in accordance with the present invention. In particular, torque tube 24, being operatively coupled to drive unit 28 is rotated. This causes rotation of the combination of flexible blades 22, and attached tip 32 about guide wire 20. In FIG. 4, rotating blades 22 are shown in a first position by solid lines. When in the first position, the flexible blades 22 are unflexed. As such, bend 42 defines a radius of cutting action from a central axis 62 indicated by the arrow 60. As shown, central axis 62 corresponds to the central axis of torque tube 24, and is the effective axis about which flexible blades 22 rotate. Drive mechanism 28 includes a control element 26 for pulling base 46 longitudinally along central axis 62 generally in the direction shown by arrow 52. This pulling action by control element 26 causes base 46 to also move in the direction of arrow 52. Consequently, this action also pulls the desmodromic filaments 44 through channels 54 of torque tube 24, and slides tip 32 into a second position as shown by dotted line 32' in FIG. 4. The amount of pull in the direction of arrow 52 is limited by stop 56 which, at position 56', abuts against end 64 of channel 54 on torque tube 24. Movement of tip 32 to its second position 32' also causes flexible blades 22 to bow outwardly and away from the guide wire and the axis of rotation 62 as shown by dotted line 22' in FIG. 4. This causes a corresponding increase in the cutting action radius 60 of blades 22 to a greater or expanded cutting action radius 60'. As can be appreciated by operation of the device, the amount of longitudinal displacement of base 46, and thus tip 32, along guide wire 20 in the direction shown by arrow 52 determines the amount of lateral displacement of bend 42 in blades 22 and the consequent increase in the cutting radius 60' achieved by the bowed flexible blades 22.

This expanded bowed cutting action can be selectively controlled by control element 26, and can even be implemented during rotation of the blades 22. It can be seen, therefore, that a smaller entry site opening in the patient can accommodate the cutting device when the blades are in their unflexed or first position. In this position, the blades 22 establish a radius which is substantially the same as that of the torque tube 24. On the other hand, once the cutting device 10 has been introduced into the vessel 14 and moved to the site of the lesion 18, the radius 60 of the cutting action can be increased to the radius 60' or any intermediate desired size to efficaciously cut away the unwanted material of lesion 18 as required. In practice, the outside diameter of torque tube 24, and thus radius 60 of the unflexed and unbowed blades 22 is approximately on the order of five French, i.e. sixty-five thousandths of an inch. Maximum displacement of the tip 32 into its position 32' increases the cutting action of blades at position 22' to increase the cutting action radius by approximately thirty percent. In addition, because of the sliding action of the tip 32 caused by desmodromic filaments 44, the cutting action can be adjusted to an infinite variety of settings over a continuous range within the minimum and maximum cutting action radii.

While the particular expandable atherectomy cutting device as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as defined in the appended claims.

I claim:

1. An expandable atherectomy cutting device comprising:
   a guide wire;
   a desmodromic wire;
   a torque tube rotatably positioned about said guide wire, said torque tube having a sidewall including a channel for slidably receiving said desmodromic wire;
   a tip rotatably positioned on said guide wire, said tip being slidable along said guide wire between a first position and a second position;
   four flexible blades spaced 90° apart, each said blade having one end connected to said torque tube and another end connected to said tip, each said flexible blade urging said tip to said first position wherein each said blade defines a first radius of cutting action; and
   means associated with said tip and said casing for urging said tip to said second position wherein each said blade defines a second radius of cutting action greater than said first radius of cutting action, said means for urging said tip to said second position comprising a base controllably movable along said torque tube, said base being connected to said tip by said desmodromic wire for drawing said tip into said second position.

2. An expandable atherectomy cutting device as recited in claim 1 wherein there is a plurality of desmodromic filaments attached equally apart.

* * * * *